United States Patent
Maurin et al.

[11] Patent Number: 5,922,972
[45] Date of Patent: Jul. 13, 1999

[54] DEVICE FOR TAKING SAMPLES ON A PIPELINE

[75] Inventors: Yves Maurin; Patrick Debelle-Duplan, both of Lyons; Charles de Castelbajac, Ecully, all of France

[73] Assignee: H+Valves, France

[21] Appl. No.: 08/853,336

[22] Filed: May 8, 1997

[30] Foreign Application Priority Data

May 10, 1996 [FR] France .................................. 96 06175

[51] Int. Cl.[6] .................................................. G01N 1/20
[52] U.S. Cl. .................................... 73/863.86; 73/863.57; 73/863.73
[58] Field of Search ........................... 73/863.86, 863.73, 73/863.57, 863.52, 863.56, 863.85, 863.83, 863.84, 864.74, 864.51

[56] References Cited

U.S. PATENT DOCUMENTS

| | | | |
|---|---|---|---|
| 2,864,254 | 12/1958 | McDonald et al. | 73/863.73 |
| 3,561,727 | 2/1971 | Scaramucci | 251/172 |
| 3,617,027 | 11/1971 | Scaramucci | 251/175 X |
| 3,744,319 | 7/1973 | Harmes, III | 73/863.86 |
| 3,784,155 | 1/1974 | Tomlin | 251/181 |
| 4,286,614 | 9/1981 | Kacal et al. | 251/174 X |
| 4,342,444 | 8/1982 | Sonderman | 251/315 |
| 4,350,052 | 9/1982 | Kendall | 73/863.86 |
| 4,472,977 | 9/1984 | Lynn | 73/863.73 X |
| 4,637,421 | 1/1987 | Stunkard | 251/317 X |
| 4,671,308 | 6/1987 | Williams et al. | 251/174 X |
| 5,070,909 | 12/1991 | Davenport | 137/625.32 |
| 5,305,986 | 4/1994 | Hunt | 251/207 |
| 5,408,890 | 4/1995 | Klaus | 73/863.86 X |

FOREIGN PATENT DOCUMENTS

| | | | |
|---|---|---|---|
| 2688046 | 9/1993 | France . | |
| 234074 | 3/1986 | German Dem. Rep. | 73/863.86 |
| 3932202 | 4/1991 | Germany . | |
| 9202623 | 6/1992 | Germany . | |
| 9401379 | 12/1994 | Germany . | |
| 9001848 | 3/1992 | Netherlands | 73/863.86 |
| 2140896 | 12/1984 | United Kingdom . | |
| 2207735 | 2/1989 | United Kingdom . | |

OTHER PUBLICATIONS

English language abstract of DE 3932202 dated Apr. 4, 1991 Copyright 1997 (month not given) Derwent Info.
*Patent Abstracts of Europe* (GB 021887078A) Oct. 7, 1987 "Fire–Safe Ball Valve" Guiseppe Bianchi, et al.
*Patent Abstracts of Japan* Grp. M1476, vol. 17, No. 497 Abs Pub Date Sep. 8, 1993 (05–124734) Yoshikawa.
*Patent Abstracts of Europe* (FR 02688046 A) Sep. 3, 1993 "Ball Valve".
*Patent Abstracts of Japan* (07–55026) dated Mar. 3, 1995 "Ball Valve" Sadeyuki Nakanishi et al.

*Primary Examiner*—Thomas P. Noland
*Attorney, Agent, or Firm*—Wall Marjama Bilinski & Burr

[57] ABSTRACT

Apparatus for obtaining a fluid sample from a flow moving through a pipeline that includes a cylindrical body mounted in the line that has the same inside diameter as the pipeline. A housing is attached to the body which communicates therewith through an orifice. A ball is rotatably mounted in the housing upon upper and lower seats with the lower seat resting on a shoulder formed in the housing at the entrance to a circular opening. The ball contains a recess and a lever that moves the ball between a first position wherein the recess is exposed to the flow through the orifice to collect a sample and a second position wherein the collected sample is released through the opening. The diameter of the opening at the entrance being less than the diameter of the ball whereby the ball will close the opening in the even the lower seal is destroyed.

6 Claims, 3 Drawing Sheets

DEVICE FOR TAKING SAMPLES ON A PIPELINE

BACKGROUND OF THE INVENTION

The invention relates to a novel device for taking samples, especially fluid and more particularly liquid, on a pipeline.

During many manufacturing or synthesizing processes in various industries, especially chemistry, petrochemistry, pharmaceuticals and agri-foodstuffs, it proves necessary to conduct one or more checks on the quality of the product being manufactured or prepared in the course of the various steps of the process in question, the purpose of this being, in particular, to arrive at a product meeting the required quality standards and thereby to avoid rejects by exerting an influence, as a function of the analyses carried out, on the parameters and the conditions implemented during the said process.

To this effect, conventional cocks are usually installed on the pipelines for transferring the products and make it possible to collect the said products manually in order to conduct an analysis of them. Apart from the fact that, with such a cock, the operator comes into direct contact with the fluid to be analysed or its vapours, which may be toxic, the quantity of liquid sampled is entirely arbitrary and, moreover, the sealing of this type of cock is often insufficient for a large number of applications.

There are flap-type or pintle-type sampling systems which are mounted on a branch of the main pipeline and which then make it possible to fill a bottle. The sealing member of the cock consists of a flap, a pintle or a cylinder; opening takes place either directly in the fluid stream or in the body of the cock by means of a wheel which releases the sealing member from its seat and allows the liquid to flow into the bottle.

This system has some disadvantages. In fact, it is necessary to have good sealing relative to the passage of the control spindle (gland) and the seat. Now this sealing is relatively difficult to obtain with regard to chemically aggressive and/or heavily laden fluids. Moreover, it deteriorates more and more in proportion to the increase in the number of operations. Finally, the bottle is subjected to the same pressure as that of the main pipe.

Finally, a device employing a system of needles, which consists of a valve, of a needle fastening and of a protective sleeve, is also provided. Two needles are provided, one for sampling and the other for escape. Such a system is mounted on the pipe by means of the connections of the valve. However, although this device makes it possible to sample a specific quantity of product to be analysed, nevertheless the said product can only be extremely clean and of very low viscosity, in view of the use of needles, the outflow orifice of which is very narrow, thus drastically reducing its applications. Furthermore, it is necessary to use a bottle equipped with a diaphragm adapted to each product, in order to ensure good sealing.

SUMMARY OF THE INVENTION

The present invention provides a device for taking samples on a pipeline, which is at once reliable and simple to use and makes it possible to sample calibrated quantities of the product. In order to give the general installation, in which it is installed, protection against fire, this device is designed according to the "fire safety" type.

This device comprises:

an in-line body capable of being installed on the pipeline, from which the sample of product is to be taken, and of being fastened to the said pipeline by means of standardized flanges (bolted or in one piece), the inside diameter of the body being identical to the inside diameter of the said pipeline, the body having, furthermore, a lateral orifice making it possible to fasten a ball cock;

a cock of the ball type, opening out into the in-line body by way of the said lateral orifice and forming one of the two parts of the body forming the cock, the other part of which is fixed to the first after an annular gasket has been put in place, the said cock comprising a recessed ball provided with a blind hole accessible via a single entrance, thus defining a calibrated volume, the said ball being capable of pivoting through 180 degrees between two annular gaskets positioned respectively at the junction between the in-line body and the upstream part of the ball cock and within the body of the said ball cock, the said ball thus being capable of communicating, on the one hand, with the in-line body at the lateral orifice and, on the other hand, with the downstream part of the cock, the said downstream part comprising a duct for outflow towards a bottle, attached removably to the body of the cock, each of the two parts receiving a seat of substantially annular shape, the said seats being intended to ensure the sealing of the cock relative to the pipeline, in the region of which the sampling is carried out, the inner profile of the second part having a shoulder which is intended to receive one of the two seats and the diameter of which is smaller than the outside diameter of the ball, so that, in the event of destruction of the seats, metal/metal or ceramic/metal contact is ensured so as to seal the assembly as a whole.

In other words, the invention involves installing, in addition to a ball cock, the ball of which is recessed, but blind, so as to define a calibrated volume, also seats of suitable shape and component elements of the body of the cock which are produced in such a way that, in the event of fire liable to bring about the destruction of the said seats, intimate contact is made between the ball and the said elements, the said contact being sufficient to ensure sealing relative to the fire in the region of the rest of the installation, in other words to give "fire safety", as will emerge, moreover, in more detail later, which has been impossible to obtain with the devices available hitherto.

According to the invention, the body of the ball cock receives two complementary inserts in the form of an annular ring, which are intended to fill the cavity of the body around the ball and thus as far as possible to reduce the possibility that fluid will infiltrate around the said ball during the sampling operation.

The seats, the inserts and the annular gasket which were mentioned above are generally produced from polytetrafluoroethylene—PTFE (TEFLON—registered trademark). However, other materials may be used, depending on the fluid to be sampled.

According to the invention, the lever for operating the cock is fixed to a spindle. The latter is shouldered and mounted via the interior of the body of the cock, in order to prevent the said spindle from being ejected accidentally.

The bottle for collecting the samples is generally screwed to a connector for fitting the bottle, the said connector itself being fixed to the body of the ball cock, the said body moreover receiving a collecting collar. The assembly as a whole is thus positioned so as to be opposite the orifice communicating with the interior of the in-line body.

The bottle may be fixed to the body of the cock by screwing or any other means of quick coupling, such as a cam-type or flange-type connection or a well-known "clamps" system.

BRIEF DESCRIPTION OF THE DRAWINGS

How the invention can be implemented and the advantages which stem from it will emerge more clearly from the following exemplary embodiment given as a non-limiting indication, with reference to the accompanying figures.

FIG. 1 is a diagrammatic perspective illustration of the device according to the invention, of which

DESCRIPTION OF THE INVENTION

Figure 1:
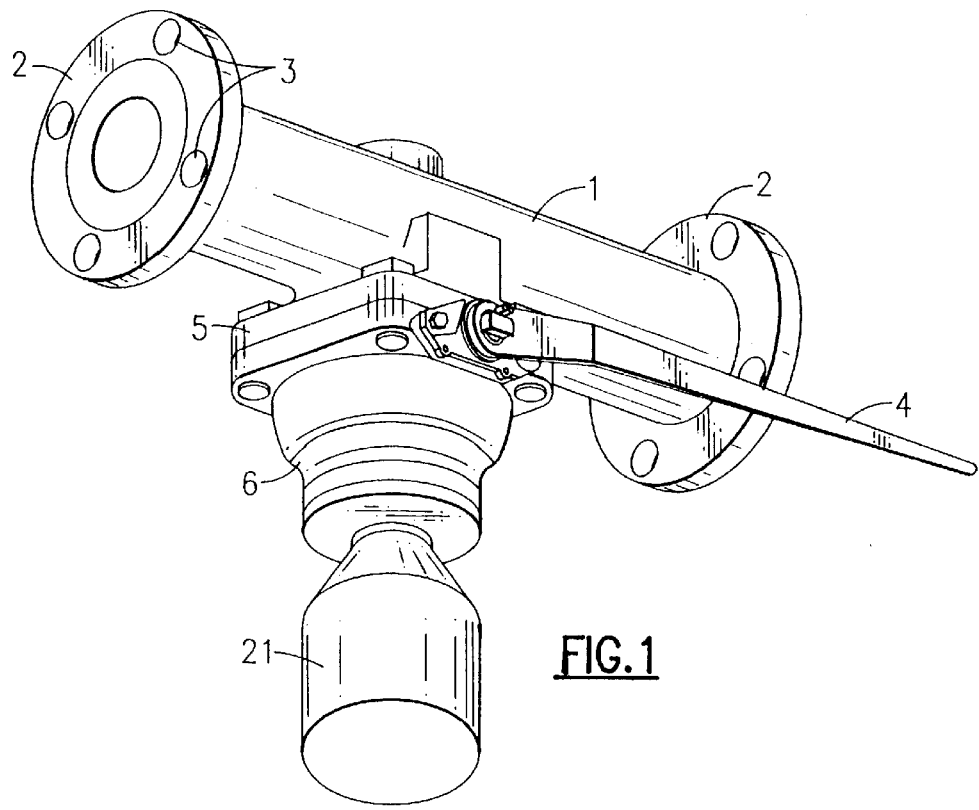
Figure 2:
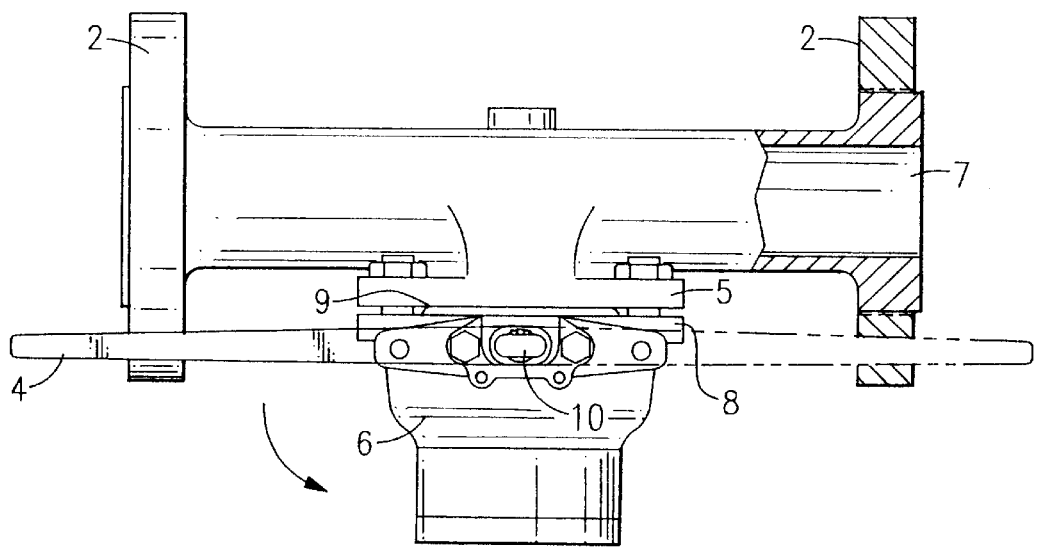
FIG. 2 is a top view.

FIG. 1 shows a diagrammatic perspective view of the device for taking samples according to the invention. This device consists, first of all, of an in-line body (1), typically consisting of a piece of pipeline and capable of being fastened to such a pipeline by means of flanges (2) pierced with passage holes (3), in order to make bolting possible. The diameter of the inner pipeline (7), which the in-line body (1) defines, is identical to that of the pipeline to which it is connected.

This in-line body (1) comprises an orifice, putting the interior of the pipeline (7) in communication with the exterior, in a fastening zone (5) made substantially in the middle of the said body and intended to form the first part of the body of a cock described in detail below. The in-line body (1)/fastening zone (5) assembly is obtained directly from casting and therefore is in one piece.

Figure 3:
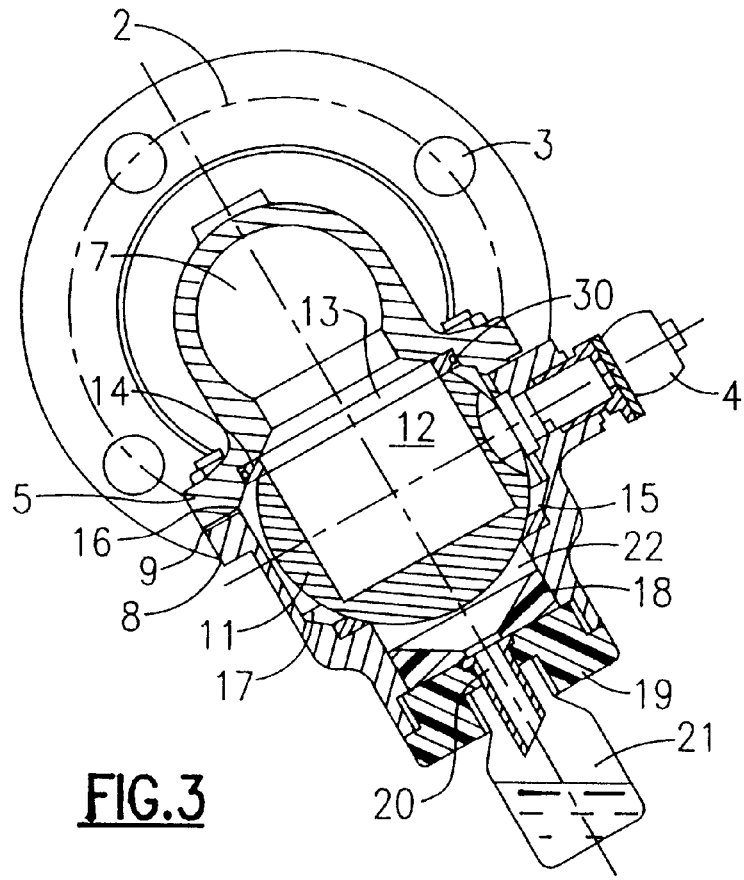
FIG. 3 is a diagrammatic cross-sectional illustration of the device according to the invention.
Figure 5:
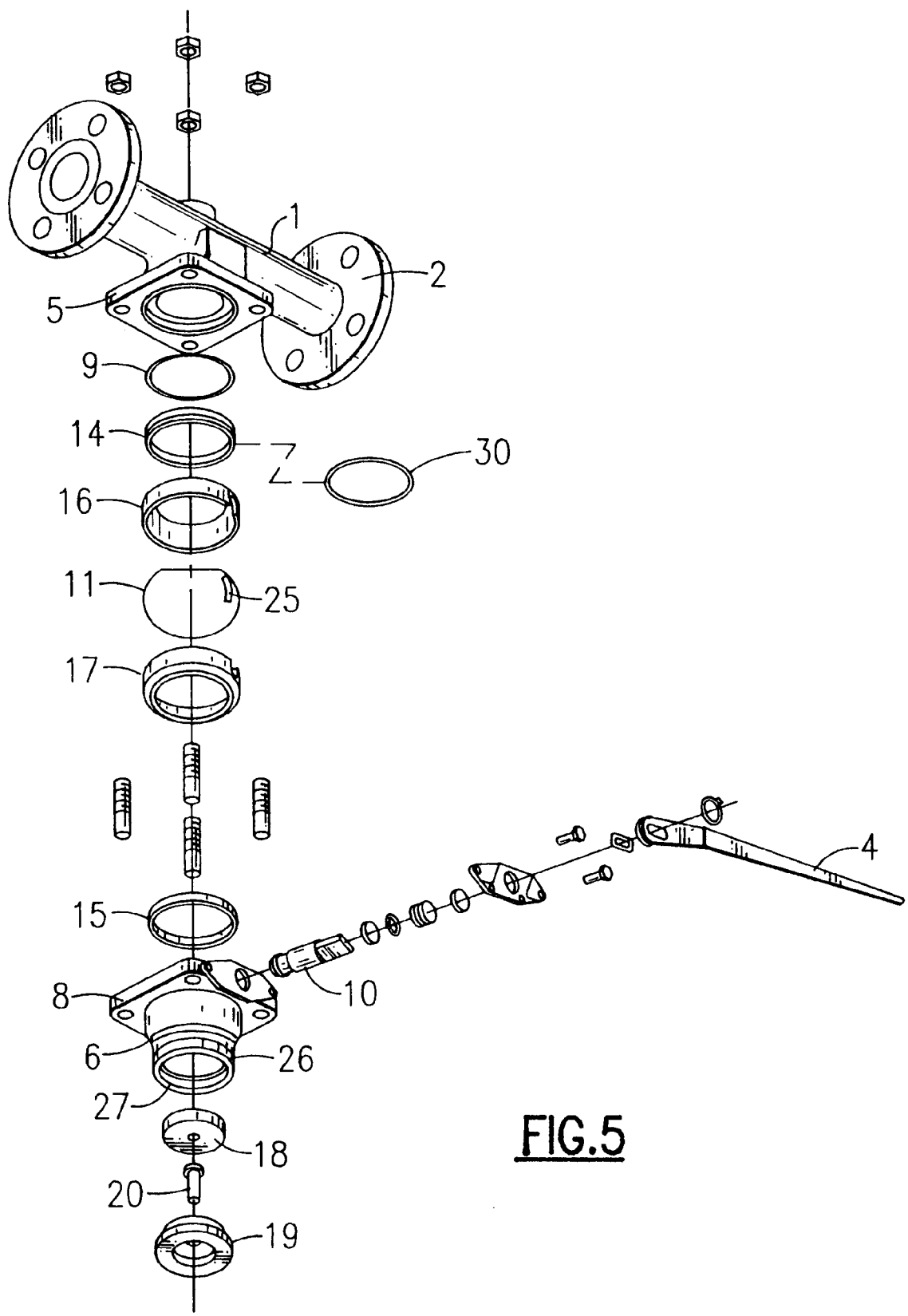
FIG. 5 is a diagrammatic exploded illustration of the device according to the invention.

A complementary piece (6) is intended to be fastened to this fastening piece (5) by means of a fastening flange (8), the said piece (6) thereby forming the second part of the body of the cock in question. Before this second part is installed on the fastening part (5), an annular gasket made from polytetrafluoroethylene (PTFE) (9) is inserted, as may be seen more clearly in FIG. 3 or FIG. 5. This gasket is intended, in a known way, to seal this junction zone. However, the gasket (9) may be produced from another material, such as, for example, graphite, for an assembly of the "fire safety" type.

The cock associated with this in-line body is a cock of the ball type, of which the ball (11), operated by means of a lever (4) and a spindle (10), is recessed in order to define a calibrated internal volume (12), the said ball (11) being open on its periphery, so as to define an entrance (13) capable of coming opposite the orifice made in the junction zone (5), that is to say opposite the pipeline (7). This ball may be produced from any material, especially from sintered ceramic or from metal. It is capable of rotating on itself through 180° under the combined effect of the spindle (10) and of the lever (4), in order to make it possible to put the content of the volume (12) which it defines in communication with a collecting device (18, 19, 20) and a recovery bottle (21), as will be described in more detail later.

The ball (11) is guided perfectly within the body (5, 6) due to the presence, on the one hand, of annular seats (14) and (15) attached respectively to the first part (5) and second part (6) of the body of the cock, in substantially diametral positions, and also by the placing of inserts (16) and (17), in the form of sectors of a ring, likewise received in the two component parts of the body, making it possible, furthermore, to limit the dead zone contained between the ball (11) and the body of the ball cock.

The seats and other inserts are generally produced from PTFE. However, other materials may be used, depending on the type of fluid flowing in the pipeline (7).

According to the invention, the downstream seat (15) is received in a shoulder (22) obtained from casting or machining and arranged within the second component part (6) of the body. As may be seen clearly in FIG. 3, this shoulder has a diameter smaller than the outside diameter of the ball (11) and is capable of coming into contact with the said ball (11) in the event of damage to the seat (15), especially in the event of destruction by fire. This results in metal/metal contact or metal/ceramic contact if the ball (11) is produced from ceramic, the said contact having some sealing in view of the pressure which, in any event, is exerted on the ball by the fluid flowing in the pipeline (7), this pressure being exerted in the direction of the container (21). This results in a device for taking samples of the "fire safety" type.

The upstream seat (14) may be of the piston type. It comprises a groove intended to receive an elastomeric O-ring seal (30) resistant to the fluids to be sampled. The assembly thus produced forms a piston which bears permanently against the ball (11) by means of the pressure of the fluid.

This system thus makes it possible to reduce the operating torque appreciably by reducing the frictional forces of the ball (11) on the upstream seat (14) very substantially, whilst at the same time ensuring complete sealing between the seats (14) and (15) and the ball (11) for the entire duration of the operation of taking samples (rotation of the ball through 180°).

According to the invention, the device comprises a receptacle for collecting the liquid thus sampled. This receptacle or bottle (21) is fastened removably to a fitting connector (19) having an internal thread corresponding to the external thread made on the neck of the said receptacle (21). This same fitting connector (19) ensures the clamping of an outlet tube (20) and of a collecting collar (18), the assembly as a whole being held against the second component part (6) of the body of the cock by screwing the said fitting connector onto an internal thread (27) made for this purpose on the part (26) which the said second part comprises, as may be seen clearly in FIG. 5.

In order to give both the collecting collar (18) and the fitting connector (19) some mechanical strength, these are generally produced from PTFE filled with glass fibre. Other materials may be used, depending on the type of fluid to be sampled.

Figure 4:
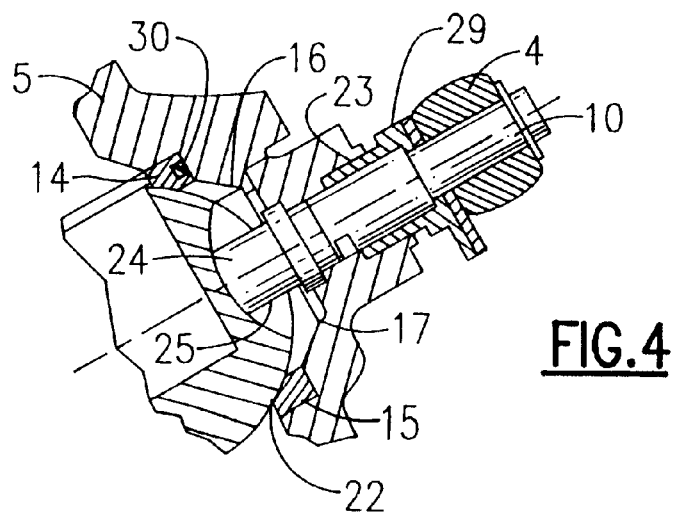
FIG. 4 is a detailed view of the mode of fastening the spindle for actuating the ball.

According to another characteristic of the invention, sealing, and more particularly the "fire safety" system developed by the device, is likewise imparted to the spindle (10) and to the lever (4) actuating the ball (11). As may be seen in FIGS. 3 and 4, this spindle (10) drives the ball (11) by means of a slot (25) made on the periphery of the latter and by means of a stud (24) coming into place in the said slot, the said spindle being mounted on the component part (6) of the body of the cock together with sealing packing consisting of a stack of several rings (23) machined in the form of herringbones, thus allowing deformation of the packing as result of the clamping of the gland (29). This packing is generally produced from PTFE. Where a "fire safety" cock is concerned, both the packing (23) and the gasket between the two parts of the body (9) consist of rings produced from graphite.

The advantages which the device according to the invention affords will be understood in the light of its structure. Of these, mention may be made, first of all, of the possibility of having a calibrated fluid volume available, as desired. For this purpose, once sampling has been carried out, it is sufficient to unscrew the bottle (21) from the connector (19) and conduct the analysis of its content, this taking place in the absence of any contact with the operator.

Moreover, by virtue of the positioning of the seats and other inserts ensuring a specific rotation of the ball of the ball cock, the assembly as a whole is completely sealed relative to the outside for the entire duration of the operation, this proving indispensable in all processes, especially in the chemical and petrochemical industries.

We claim:

1. Apparatus for obtaining a fluid sample from a flow moving through a pipeline that includes a cylindrical body having fastening means for connecting the body into a pipeline in axial alignment therewith, the inside diameter of the body being substantially equal to that of the pipeline, a housing attached to said body which opens into said body through an orifice, a ball rotatably contained in said housing within a two-piece seat that includes an annular upper seat surrounding the orifice and a lower annular seat that is mounted upon a shoulder in the housing surrounding the entrance of a circular opening, said ball further containing a recess having a given volume, said housing contains two complementary inserts in the form of rings which surround the ball to fill a space between the two seats to prevent fluid from passing between the housing and the ball;

lever means for moving the ball from a first position wherein the recess communicates with the body through said orifice to collect a fluid sample to a second position wherein the collected sample is released from the recess through said opening, and said opening at the entrance having a diameter that is smaller than the outside diameter of the ball so that the ball is capable of sealing against the shoulder in the event the lower seat is destroyed.

2. The apparatus of claim 1 wherein the upper seat includes an O-ring which is contained in a groove formed in the housing, said O-ring being resistant to the fluids being sampled, said O-ring being exposed to said fluid in said body to place the O-ring in pressure contact against the ball.

3. The apparatus of claim 1 wherein the seats and inserts are formed of polytetrafluoroethylene.

4. The apparatus of claim 1 wherein said lever means for rotating said ball includes a spindle secured in said housing and packing means compressed upon said spindle which acts upon the housing to seal said spindle.

5. The apparatus of claim 1 that further includes a sample collecting bottle that is threadably received in a connection in said housing for collecting a sample released through said opening.

6. The apparatus of claim 1 wherein said shoulder has a diameter smaller than the outside diameter of the ball and is capable of coming into contact with said ball in the event of damage to the seat.

* * * * *